(12) United States Patent
Watson

(10) Patent No.: US 11,659,647 B2
(45) Date of Patent: *May 23, 2023

(54) HARMONIC COLD PLASMA DEVICE AND ASSOCIATED METHODS

(71) Applicant: Plasmology4, Inc., Scottsdale, AZ (US)

(72) Inventor: Gregory A. Watson, Lake Mary, FL (US)

(73) Assignee: PLASMOLOGY4, INC., Scottsdale, AZ (US)

( * ) Notice: Subject to any disclaimer, the term of this patent is extended or adjusted under 35 U.S.C. 154(b) by 53 days.

This patent is subject to a terminal disclaimer.

(21) Appl. No.: 17/323,130

(22) Filed: May 18, 2021

(65) Prior Publication Data

US 2021/0385936 A1    Dec. 9, 2021

Related U.S. Application Data

(60) Continuation of application No. 16/883,049, filed on May 26, 2020, now Pat. No. 11,019,716, which is a
(Continued)

(51) Int. Cl.
*H05H 1/46* (2006.01)
*A61L 2/00* (2006.01)
(Continued)

(52) U.S. Cl.
CPC .............. *H05H 1/46* (2013.01); *A61L 2/0011* (2013.01); *A61N 1/44* (2013.01); *A61L 2202/11* (2013.01); *H05H 1/466* (2021.05); *H05H 1/4652* (2021.05); *H05H 1/4697* (2021.05); *H05H 2240/20* (2013.01); *H05H 2277/10* (2013.01)

(58) Field of Classification Search
None
See application file for complete search history.

(56) References Cited

U.S. PATENT DOCUMENTS 6,396,214 B1 * 5/2002 Grosse ..................... H05H 1/30
                                                        315/111.41
6,406,759 B1 * 6/2002 Roth ...................... H05H 1/466
                                                        134/1.1
(Continued)

*Primary Examiner* — Srinivas Sathiraju
(74) *Attorney, Agent, or Firm* — Ballard Spahr LLP

(57) ABSTRACT

A method for generating atmospheric pressure cold plasma inside a hand-held unit discharges cold plasma with simultaneously different rf wavelengths and their harmonies. The unit includes an rf tuning network that is powered by a low-voltage power supply connected to a series of high-voltage coils and capacitors. The rf energy signal is transferred to a primary containment chamber and dispersed through an electrode plate network of various sizes and thicknesses to create multiple frequencies. Helium gas is introduced into the first primary containment chamber, where electron separation is initiated. The energized gas flows into a secondary magnetic compression chamber, where a balanced frequency network grid with capacitance creates the final electron separation, which is inverted magnetically and exits through an orifice with a nozzle. The cold plasma thus generated has been shown to be capable of accelerating a healing process in flesh wounds on animal laboratory specimens.

20 Claims, 9 Drawing Sheets

Related U.S. Application Data continuation of application No. 16/140,998, filed on Sep. 25, 2018, now Pat. No. 10,674,594, which is a continuation of application No. 15/392,400, filed on Dec. 28, 2016, now Pat. No. 10,085,335, which is a continuation of application No. 14/462,478, filed on Aug. 18, 2014, now Pat. No. 9,538,630, which is a continuation of application No. 13/149,744, filed on May 31, 2011, now Pat. No. 8,810,134, which is a continuation of application No. 12/638,161, filed on Dec. 15, 2009, now Pat. No. 8,005,548, which is a division of application No. 12/038,159, filed on Feb. 27, 2008, now Pat. No. 7,633,231.

(60) Provisional application No. 60/913,369, filed on Apr. 23, 2007.

(51) Int. Cl.
*A61N 1/44* (2006.01)
*H05H 1/24* (2006.01)

(56) References Cited

U.S. PATENT DOCUMENTS

| | | | | |
|---|---|---|---|---|
| 6,958,063 B1* | 10/2005 | Soll | | A61B 18/042 606/49 |
| 7,271,363 B2* | 9/2007 | Lee | | H05H 1/46 219/121.36 |
| 7,589,473 B2* | 9/2009 | Suslov | | H05H 1/42 315/111.21 |
| 7,589,949 B2* | 9/2009 | Salisbury | | H01T 19/04 361/231 |
| 7,608,839 B2* | 10/2009 | Coulombe | | H05H 1/48 606/41 |
| 7,633,231 B2* | 12/2009 | Watson | | A61N 1/44 219/121.36 |
| 7,815,638 B2* | 10/2010 | Farin | | A61B 18/042 606/41 |
| 7,928,338 B2* | 4/2011 | Suslov | | C23C 4/134 219/121.48 |
| 8,005,548 B2* | 8/2011 | Watson | | A61L 2/0011 606/41 |
| 8,810,134 B2* | 8/2014 | Watson | | H05H 1/46 315/111.41 |
| 8,928,230 B2* | 1/2015 | Watson | | A61M 16/12 315/111.21 |
| 9,006,976 B2* | 4/2015 | Watson | | A61L 2/00 315/111.21 |
| 9,080,982 B1* | 7/2015 | Asprey | | G01N 21/68 |
| 9,192,776 B2* | 11/2015 | Hummel | | H05H 1/46 |
| 9,257,264 B2* | 2/2016 | Hummel | | H01J 37/32348 |
| 9,295,280 B2* | 3/2016 | Jacofsky | | A61L 2/14 |
| 9,384,947 B2* | 7/2016 | Watson | | A61N 1/44 |
| 9,418,820 B2* | 8/2016 | Watson | | A61L 2/0011 |
| 9,437,401 B2* | 9/2016 | Watson | | H05H 1/2406 |
| 9,472,382 B2* | 10/2016 | Jacofsky | | H01J 37/3244 |
| 9,498,637 B2* | 11/2016 | Sanders | | A61B 18/042 |
| 9,515,633 B1* | 12/2016 | Long | | H03H 7/48 |
| 9,521,736 B2* | 12/2016 | Jacofsky | | A61N 1/44 |
| 9,538,630 B2* | 1/2017 | Watson | | H05H 1/46 |
| 9,558,918 B2* | 1/2017 | Watson | | H01J 37/32348 |
| 9,570,273 B2* | 2/2017 | Watson | | A61L 2/0011 |
| 9,646,808 B2* | 5/2017 | Jacofsky | | A61B 18/042 |
| 9,656,095 B2* | 5/2017 | Watson | | A61M 15/02 |
| 9,861,829 B2* | 1/2018 | Jacofsky | | A61B 17/3421 |
| 9,913,358 B2* | 3/2018 | Suslov | | H05H 1/34 |
| 10,039,927 B2* | 8/2018 | Watson | | H05H 1/2406 |
| 10,064,263 B2* | 8/2018 | Watson | | H05H 1/46 |
| 10,085,335 B2* | 9/2018 | Watson | | A61N 1/44 |
| 10,674,594 B2* | 6/2020 | Watson | | H05H 1/46 |
| 2006/0081565 A1* | 4/2006 | Lee | | H05H 1/46 219/121.43 |
| 2008/0185366 A1* | 8/2008 | Suslov | | H05H 1/34 219/121.47 |
| 2013/0068732 A1* | 3/2013 | Watson | | A61M 16/12 219/121.59 |
| 2013/0072859 A1* | 3/2013 | Watson | | A61N 1/44 604/23 |
| 2013/0072860 A1* | 3/2013 | Watson | | H05H 1/46 604/23 |
| 2013/0072861 A1* | 3/2013 | Watson | | A61M 16/06 604/23 |
| 2014/0184072 A1* | 7/2014 | Jacofsky | | A61B 18/042 315/111.21 |
| 2014/0188037 A1* | 7/2014 | Jacofsky | | H05H 1/2406 604/23 |
| 2014/0188071 A1* | 7/2014 | Jacofsky | | A61N 1/327 604/501 |
| 2014/0188097 A1* | 7/2014 | Watson | | A61B 18/042 606/18 |
| 2015/0127079 A1* | 5/2015 | Watson | | H01J 37/3266 607/104 |
| 2015/0221476 A1* | 8/2015 | Watson | | A61L 2/14 315/111.21 |
| 2016/0354614 A1* | 12/2016 | Watson | | A61M 16/12 |
| 2017/0087372 A1* | 3/2017 | Jacofsky | | A61B 17/3421 |
| 2017/0111987 A1* | 4/2017 | Watson | | A61L 2/0011 |
| 2017/0136253 A1* | 5/2017 | Watson | | A61L 2/0011 |
| 2017/0156200 A1* | 6/2017 | Watson | | A61L 2/14 |
| 2020/0359490 A1* | 11/2020 | Watson | | A61N 1/44 |

* cited by examiner

HARMONIC COLD PLASMA DEVICE AND ASSOCIATED METHODS

CROSS-REFERENCE TO RELATED APPLICATIONS

This application is a continuation of U.S. patent application Ser. No. 16/883,049, filed May 26, 2020, which is a continuation of U.S. Patent Application Ser. No. 16/140,998, filed Sep. 25, 2015, which is a continuation of U.S. Patent Application Ser. No. 15/392,400, filed. Dec. 28, 2016, now U.S. Patent No. 10,0895,335, issued Sep. 25, 2018, which is a continuation of U.S. Patent Application Ser. No. 14/462,478, filed Aug. 18, 2014, now U.S. Pat. No. 9,538,630, issued Jan. 3.2017, which is a continuation of U.S. patent application Ser. No. 13/149,744, filed May 31, 2011, now U.S. Pat. No. 8,810,134, issued Aug. 19, 2014, which is a continuation of U.S. Patent Application Ser. No. 12/638,161, filed Dec. 15/2009, now U.S. Pat. No. 8,005,548, issued Aug. 23, 2011, which is a divisional of U.S. Patent Application Ser. No. 12/038,159, filed Feb. 27, 2008, now U.S. Pat. No. 7,633,231, issued Dec. 15, 2009, which claims the benefit of U.S. Provisional Application No. 60/913,369, filed Apr. 23, 2007, each of which are herein incorporated by reference in their entireties.

BACKGROUND OF THE INVENTION

Field of the Invention

The present invention relates to devices and methods for creating cold plasmas, and, more particularly, to such devices that are hand-held and methods for using same.

Description of Related Art

Atmospheric pressure hot plasmas are known to exist in nature. For example, lightning is an example of a dc arc (hot) plasma. Many dc arc plasma applications have been achieved in various manufacturing processes, for example, for use in forming surface coatings. Atmospheric pressure cold plasma processes are also known in the art. Most of the low-pressure cold plasma processes are known to utilize positive to negative electrodes in different configurations, which release free electrons in a noble gas medium.

Device that use a positive to negative electrode configuration to form a cold plasma from noble gases (helium, argon, etc.) have frequently exhibited electrode degradation and overheating difficulties through continuous device operation. The process conditions for enabling a dense cold plasma electron population without electrode degradation and/or overheating are difficult to achieve.

Therefore, it would be beneficial to provide a device for producing a cold plasma that overcomes the difficulties inherent in prior known devices.

BRIEF SUMMARY OF THE INVENTION

The device of the present invention provides streaming atmospheric pressure cold plasma inside a hand-held unit without the use of a negative electrode configuration. The device is capable of discharging cold plasma (65-69° F.) into ambient air with simultaneously different rf wavelengths and their harmonics.

The device comprises an rf tuning network that is powered by a low-voltage power supply connected to a series of high-voltage coils and capacitors that are networked to produce a 150-kV dielectric rf signal. The rf energy signal is transferred to the cold plasma device through a protected cable that allows the electrical energy to be transferred without any substantial corona discharge energy loss. The rf energy signal is transferred to a housing having an interior space defined by a wall, and dispersed through an electrode comprising a plurality of plates positioned in substantially parallel, spaced-apart fashion within the inner space. The electrode plates are supported by a support rod that is in signal communication with a source of radio frequency energy. The rod extends through each of the plates and supports a distance therebetween. A surface area of an upstream plate is greater than a surface area of a downstream plate, and the plates have various thicknesses to create multiple frequencies.

Helium gas can be introduced into the inner space upstream of the plates, where electron separation is initiated. The energized gas flows downstream into a magnetic compression chamber, comprising a first toroidal magnet having a first alignment positioned within the inner space downstream of the plates and a second toroidal magnet having a second alignment opposite the first alignment positioned within the inner space downstream of the first magnet. The first and the second magnets are substantially parallel and coaxial, and each has a central orifice.

A support is positioned between the first and the second magnet, the support having an aperture therethrough. Affixed to the support is an induction grid in frequency harmony with the electrode. The grid comprises a central capacitance element placeable in electrical communication with a source of power, and a plurality of metal rods, each having a capacitance element affixed at opposed ends. The rods are approximately symmetrically arrayed about the central capacitance element, two outermost metal rods placeable in electrical communication with the power source.

In this device gas entering the inner space is energized by the electrode, is channeled through the first magnet orifice, and contacts the grid to further energize the gas and create a multiple-frequency cold plasma thereby. A balanced frequency network grid with capacitance creates the final electron separation, which is inverted magnetically and exits out the housing through an orifice with a nozzle.

The cold plasma thus generated has been shown to be capable of facilitating and accelerating a healing process in flesh wounds on animal laboratory specimens, and to kill bacteria in vitro.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE INVENTION

Figure 1:
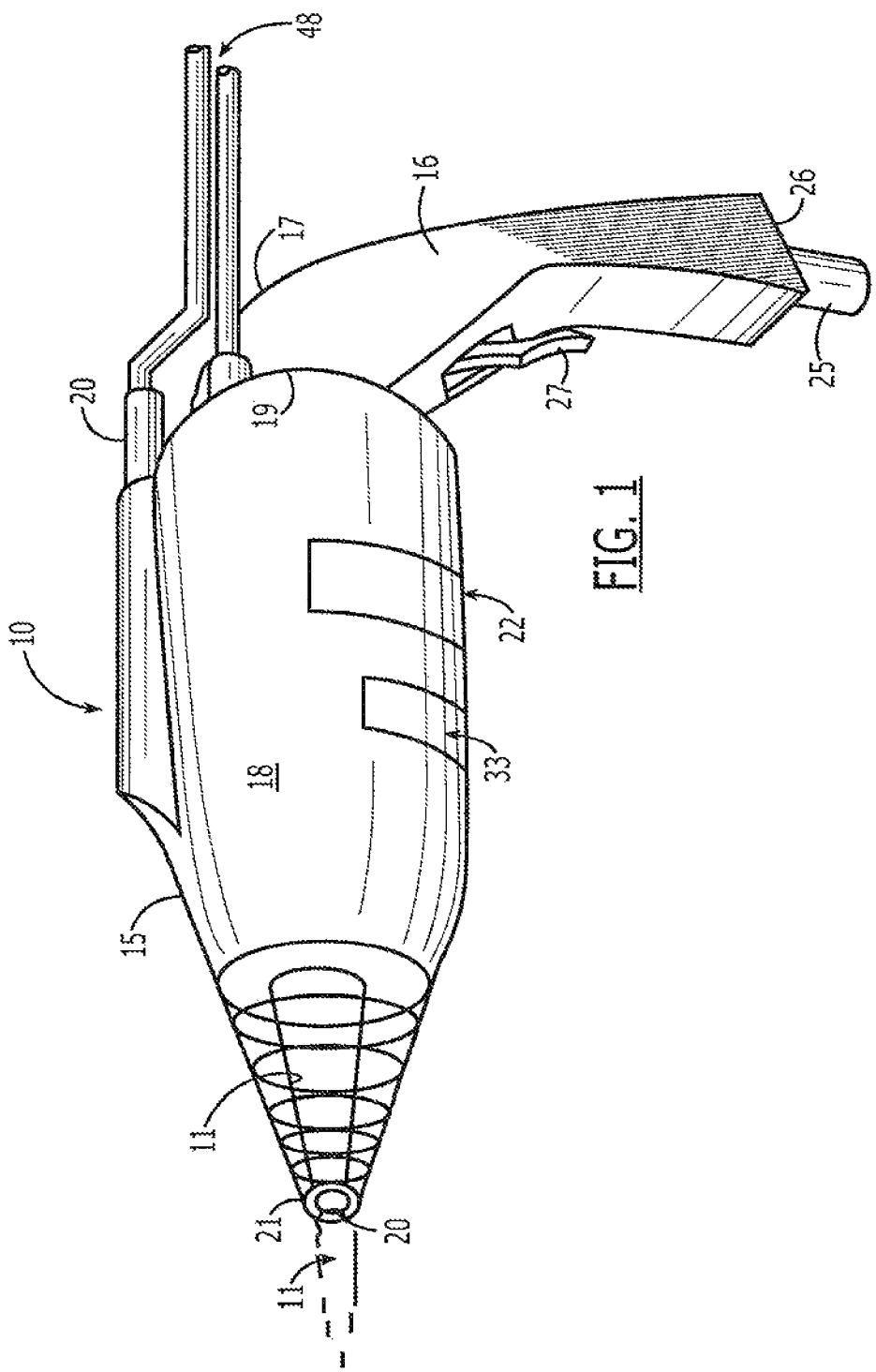
FIG. 1 is a perspective view of a hand-held atmospheric pressure multiple-frequency cold plasma source in accordance with the present invention.
Figure 2:
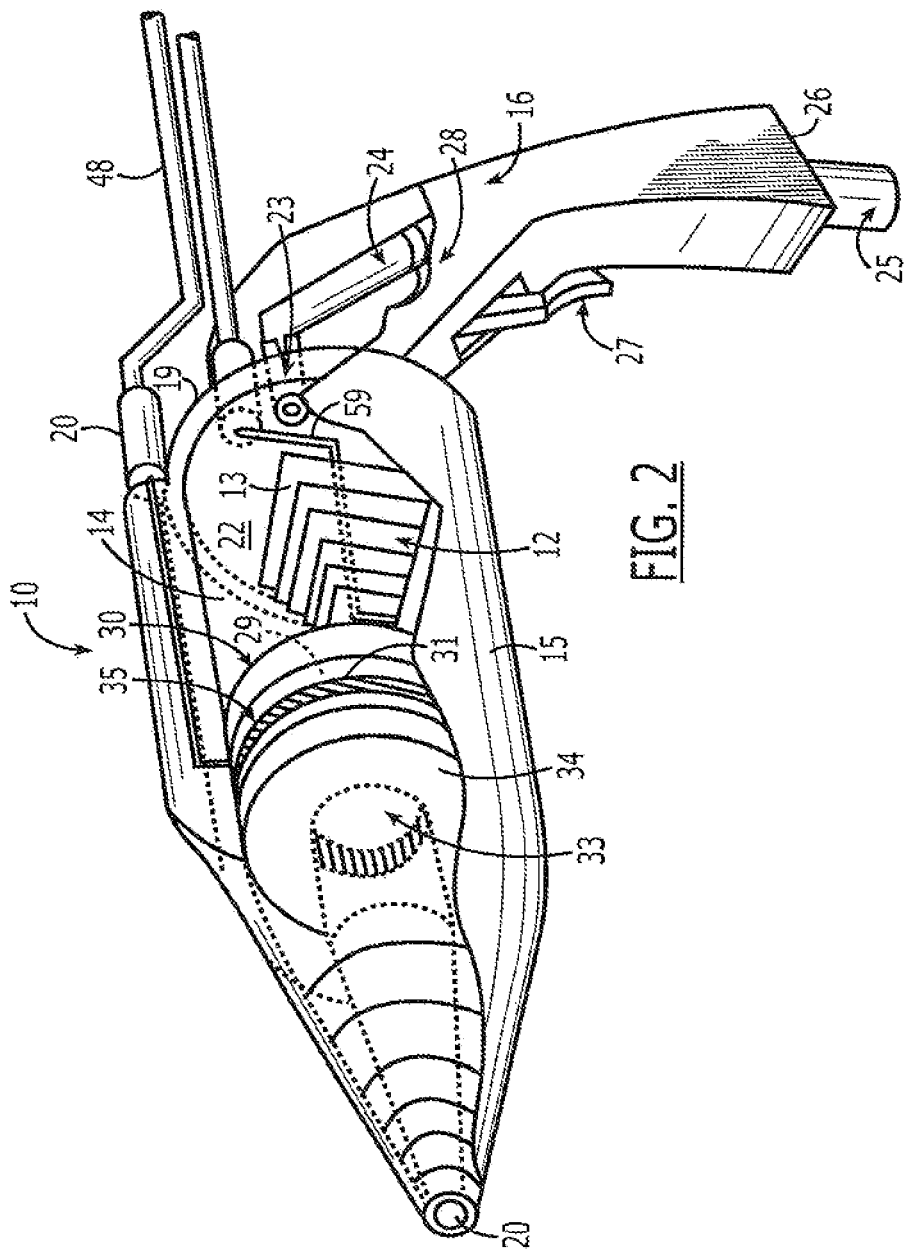
FIG. 2 is a cutaway view of the hand-held atmospheric pressure multiple-frequency cold plasma source of FIG. 1.
Figure 3:
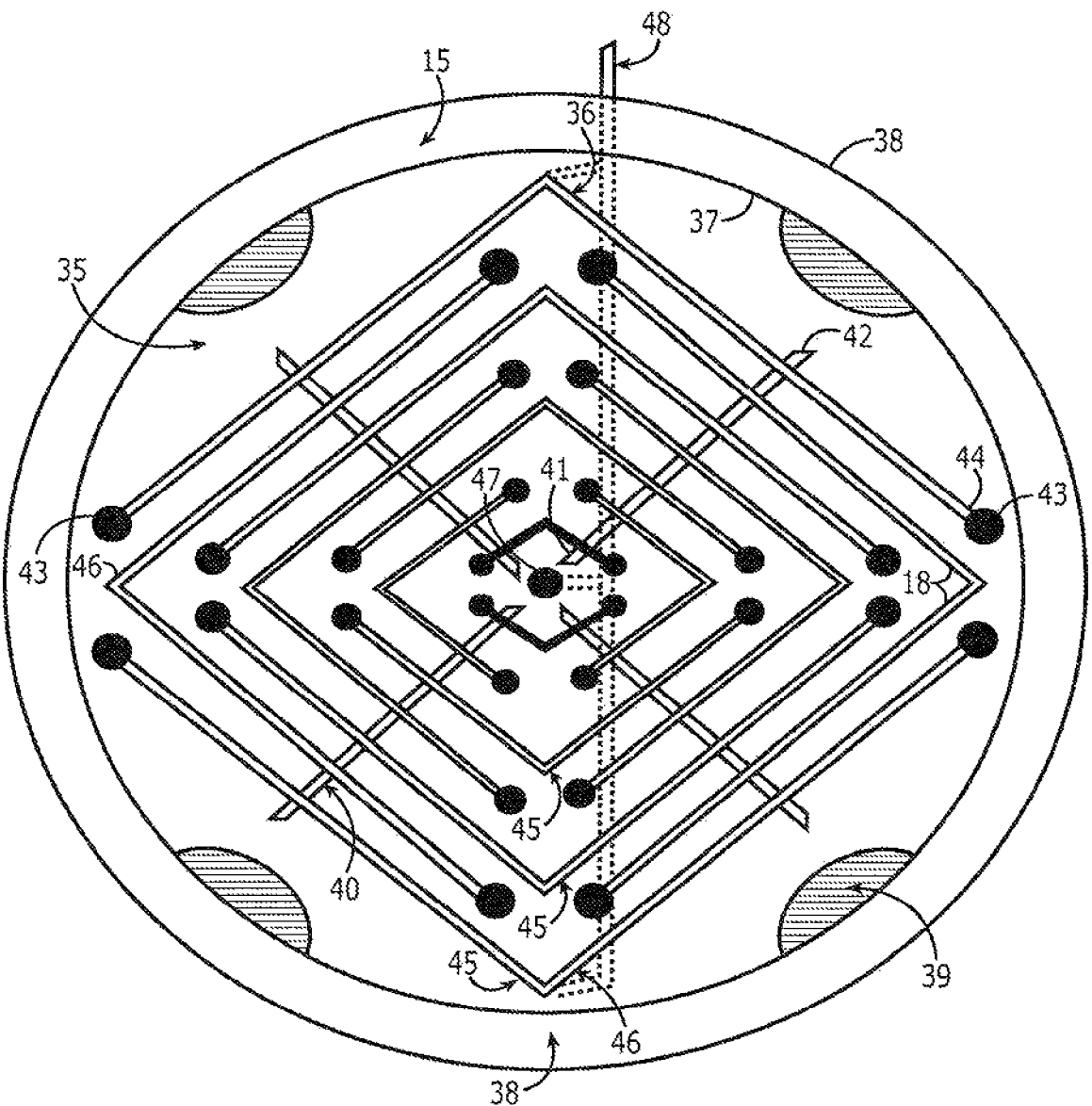
FIG. 3 is a top plan view of the rf energy induction grid of capacitance on an acrylic separation plate with balanced quad (plasma) discharge ports.
Figure 4:
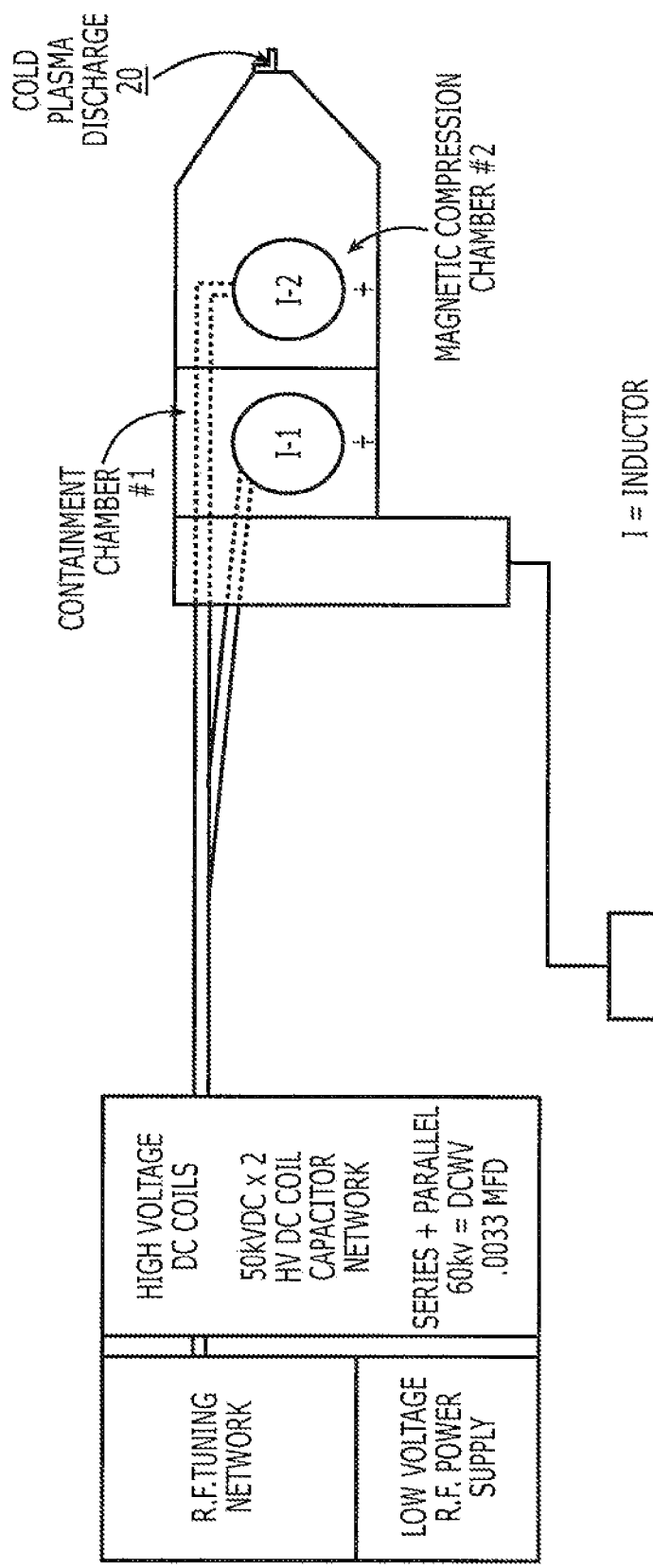
FIG. 4 is the equivalent electrical diagram that connects the power supply and tuning source to the cold plasma discharge source.
Figure 5:
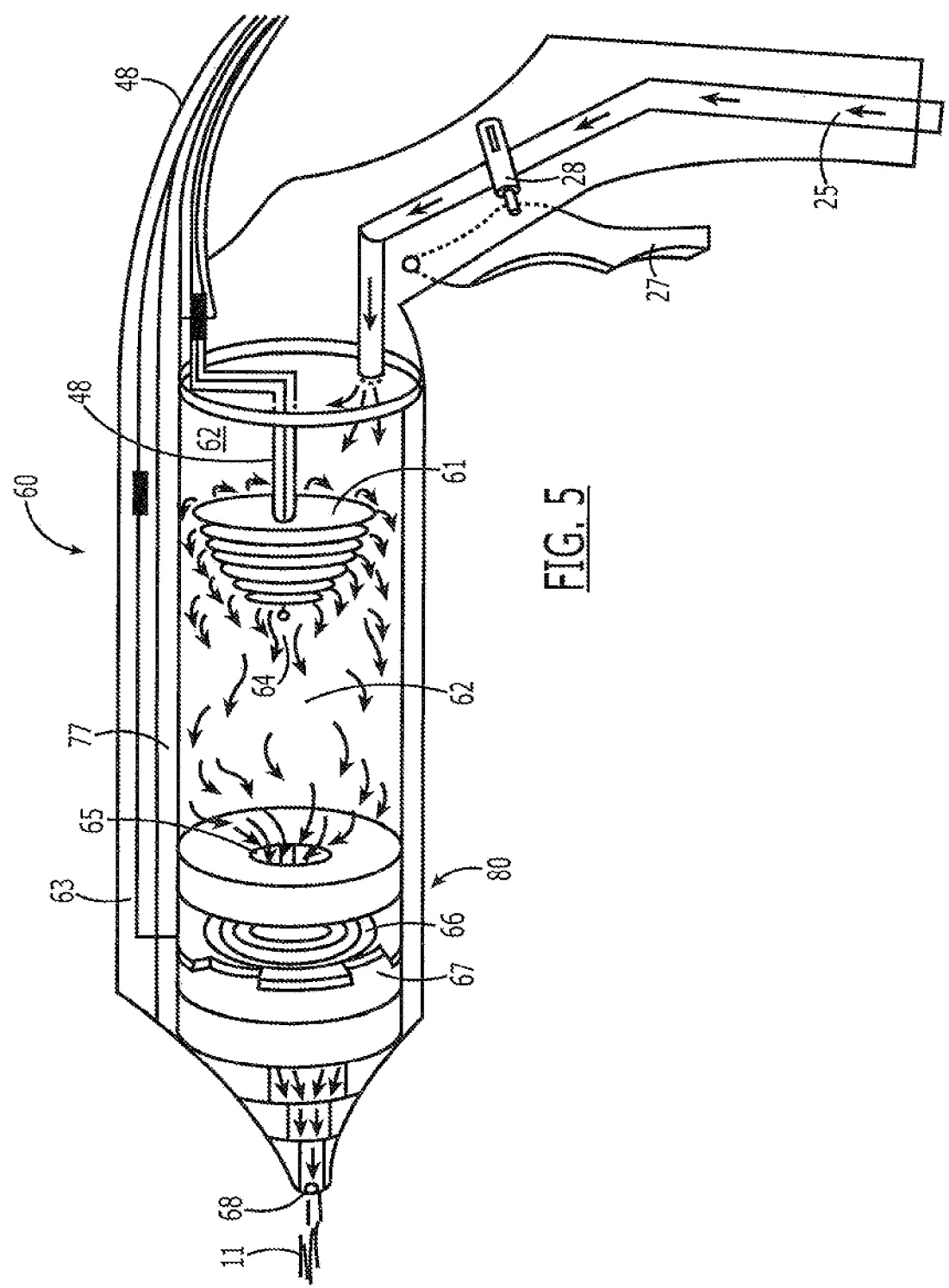
FIG. 5 is a cutaway view of a second embodiment of a hand-held cold plasma source.
Figure 6:
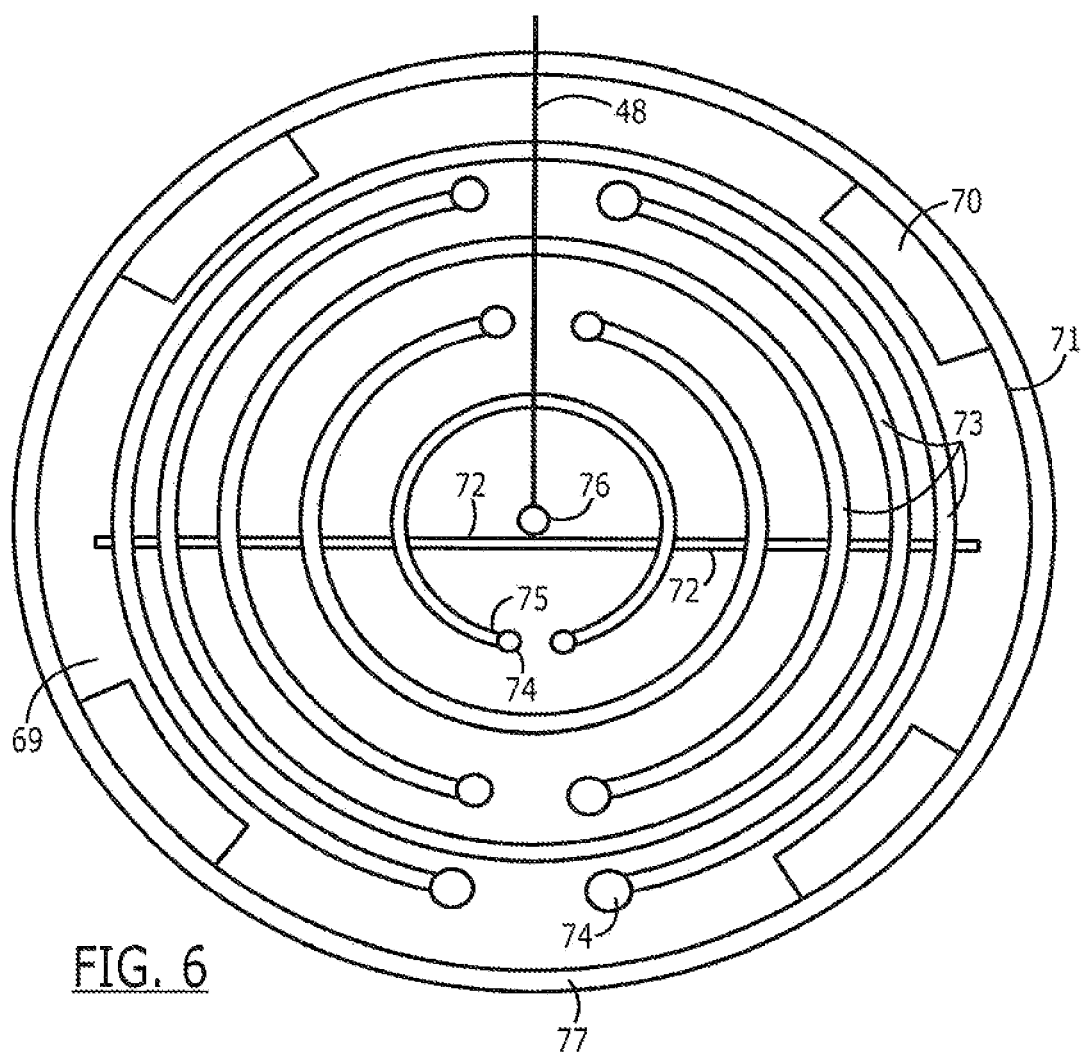
FIG. 6 is a top plan view of an induction grid for the device of FIG. 5.
Figure 7:
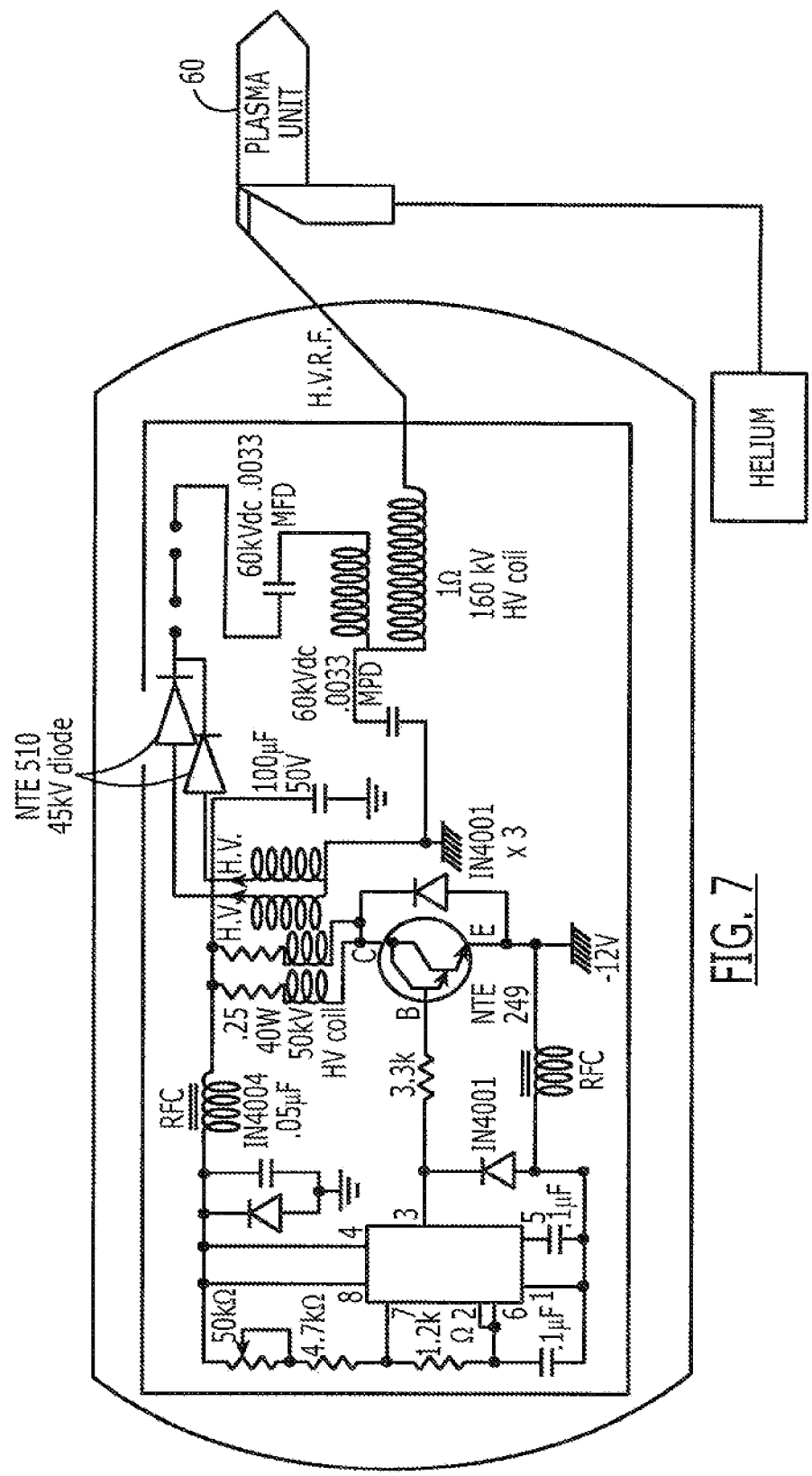
FIG. 7 is an exemplary circuit diagram for the device of FIG. 5.

A description of the preferred embodiments of the present invention will now be presented with reference to FIGS. 1-10.

The present invention is directed in a particular embodiment to a hand-held atmospheric pressure cold plasma device 10 (FIGS. 1-4) that produces multiple-frequency cold plasma 11 without the use of internal ground electrodes. The cold plasma 11 is induced through the use of multiple-frequency energy wavelengths, which are created through an electrode 12 comprising a plurality, here, seven, different-sized square brass plates 13 having a range of thicknesses from 0.001 to 0.007 in., and arranged in substantially parallel fashion, with a common central axis. The electrode 12 is positioned within an interior space 14 of a housing 15 that can have a "gun"-type shape, although this is not intended as a limitation, with a lower portion comprising a downwardly depending handle 16 meeting at a top end 17 thereof an upper portion comprising a housing body 18 that is substantially cylindrical at a proximal end 19 and tapers downward to a discharge nozzle 20 at a distal end 21. In a particular embodiment, the housing 15 has a 2.25-in. outer diameter and a 1.75-in. inner diameter in a central portion comprising the primary 22 and a secondary 33 chamber.

The plates 13 are connected together in a primary chamber 22 within the housing 15 with a substantially central brass support rod 59 connected to an rf source to maintain a predetermined distance, for example, approximately 0.125 in., between the plates 13 for multiple frequency generation. The multiple frequency electrode 12 is nickel, silver, and gold plated to induce a capacitance of energy before releasing a multiple-frequency output in the primary chamber 22 with helium gas to gain maximum separations of electrons. The helium gas is introduced into the primary chamber 22 via a gas inlet 23 positioned adjacent the proximal end 19 of the housing 15. The gas inlet 23 comprises the terminus of a tube 24 that runs through the handle 16 and terminates at a gas port 25 adjacent a bottom end 26 of the handle 16. Gas flow is controlled with a "trigger" 27, which is connected in operative relation to a gas flow valve 28 within the tube 24.

The energized gas is channeled from the primary chamber 22 through a substantially cylindrical orifice 29 in a first magnet comprising a north alignment permanent magnet 30, and exits into a space 31. The magnetic field in a secondary chamber 33 comprises a compressed magnetic field created by a second magnet comprising a south alignment permanent magnet 34, which creates a south-to-south alignment compression magnetic field. Inside the secondary chamber 33, in a position approximately in the middle of the compressed magnetic field, is positioned a magnetically inert support plate 35 comprising, for example, polymethyl methacrylate (acrylic), that contains, on a proximal side, a multiple-frequency grid system 36 (FIG. 3) that is energized through induction.

In a particular embodiment, the acrylic support plate 35 comprises a disc approximately 0.25 in. thick.

The acrylic support plate 35 has a plurality, here, four ports 39 therethrough, evenly spaced about and adjacent the circumference 37. The acrylic support plate 35 further has affixed thereto a plurality, here, four, grid supports 40, which in this exemplary embodiment are positioned approximately 90° apart, each terminating in spaced relation at their inner ends 41 from a centerpoint of the support plate 35, and in spaced relation at their outer ends 42 from the disc's circumference 37.

The "working" elements of the grid system 36 itself comprise a plurality of, here, 28, nickel, silver, and gold-plated brass capacitance spheres 43 affixed at opposed ends 44 of a plurality of, here, 14, nickel, silver, and gold-plated solid brass rods 45. In this embodiment, the rods 45 each have two substantially equal-length arms 81 and a central, inwardly facing 90° bend 46. The rods 45 are arrayed in pairs so that the spheres 43 of one rod 45 are closely opposed to the spheres 43 of a partner rod 45. There are in this embodiment seven such pairs. Each adjacent pair is arrayed so that an opposing set of spheres 43 is adjacent at least one bend 46 of the closest rod 45, so that, in plan view, the grid 36 appears as a set of nested squares with alternately interrupted corners, at the spheres' locations. The spheres 43 decrease in size from the outermost to the innermost spheres 43. At the center of the grid 36 is positioned a unitary central sphere 47, which is larger than the spheres 43 to which it is most closely adjacent.

The grid system 36 is powered by an rf power feed 48 that enters the housing 15 adjacent the housing's proximal end 19 thereof through a coupling 20. The rf power feed 48 terminates at the center sphere 47, and also at the outermost, seventh-level, bends 46.

It is believed that this type of frequency induction grid is superior in capacitance to the commonly used concentric rings of capacitance because it contains more than twice as many electrical capacitance spheres to hold and release rf energy signals, and can produce a multiple-frequency wave output. The grid 36 is constructed in frequency harmony with the multiple frequency electrode 12 positioned within the primary chamber 22, which work in concert to create a multiple-frequency harmonics. As the energized gas comes in contact with the grid 36, more electrons are energized. This highly energized gas is forced through the quad ports 39 in the acrylic plate 35. As the energized gas travels through the quad ports 39, the electron orientation is reversed 180° in south-to-south compression magnetic fields to establish a higher kinetic energy value of 15 Vdc and forced through the south-to-north magnetic field alignment to be discharged from the secondary chamber 33. The energized gas is forced out through a graduated 5-in. nozzle 20.

In use, the cold plasma can be applied directly (at a distance of 1-1.5 in.) to a living body of capacitance (e.g., laboratory specimens) to complete the circuit. The multiple-frequency cold plasma 11 that comes in contact with the tissue ranges between 65 and 69° F.

The device 10 of the present invention, which is believed at the time of filing to represent the best embodiment, can produce an atmospheric pressure cold plasma without the use of internal negative electrodes, allowing the device to operate for extended periods of time without overheating. With the length of the discharge nozzle 20 and the composition of the multiple-frequency harmonic field, a cold plasma stream 11 can be realized that can be utilized in the treatment of animal flesh wounds to accelerate healing (wound healing time in a laboratory setting has been reduced by two-thirds of normal healing time) and substantially eliminate bacterial wound infections.

Another feature of the present device 10 is its ability to remove physical pain from animal and human flesh wounds. The ability of accelerated healing time in animal flesh wounds, and the substantial elimination of bacterial infection and pain in wounds, demonstrates a novel path that may be pursued in health care for animals and humans.

To achieve a low-temperature dense (cold) plasma electron population, a dual-chamber device with a positive multiple-frequency electrode configuration allows for electron population production to create the conductive plasma flow to a body having a capacitance.

In an alternate embodiment 60 of the invention (FIGS. 5-7), a plurality of, here seven, plates 61 comprise non-insulated nickel-plated discs having decreasing diameters from the proximal to the distal end of the stack. The plates 61 are positioned within a first chamber 62 within a housing 63. The generated cold plasma 64 passes into a second chamber 80 containing a first, north magnet 65, a harmonic ring system 66, and a second, south magnet 67 before passing out the orifice 68.

In this embodiment 60, the resonator comprises a concentric ring resonator that includes an acrylic support plate 69 surrounded by a 0.25-in. acrylic tube wall 77. Four outlet ports 70 are positioned around the periphery 71 of the support plate 69, and a ring support 72 extends across the support plate 69 generally through the center thereof. A plurality of, here, six, concentric brass partial rings 73 are positioned on the support plate 69, each again having a nickel-plated brass sphere 74 affixed to ends 75 thereof that are closely opposed. The rings 73 are positioned so that each adjacent ring's ends 75 are 180° opposed to each other. A central unitary sphere 76 is also positioned on the support plate 69. Radio frequency input 48 is supplied to the central sphere 76 and to the outermost ring 73.

Figure 8:
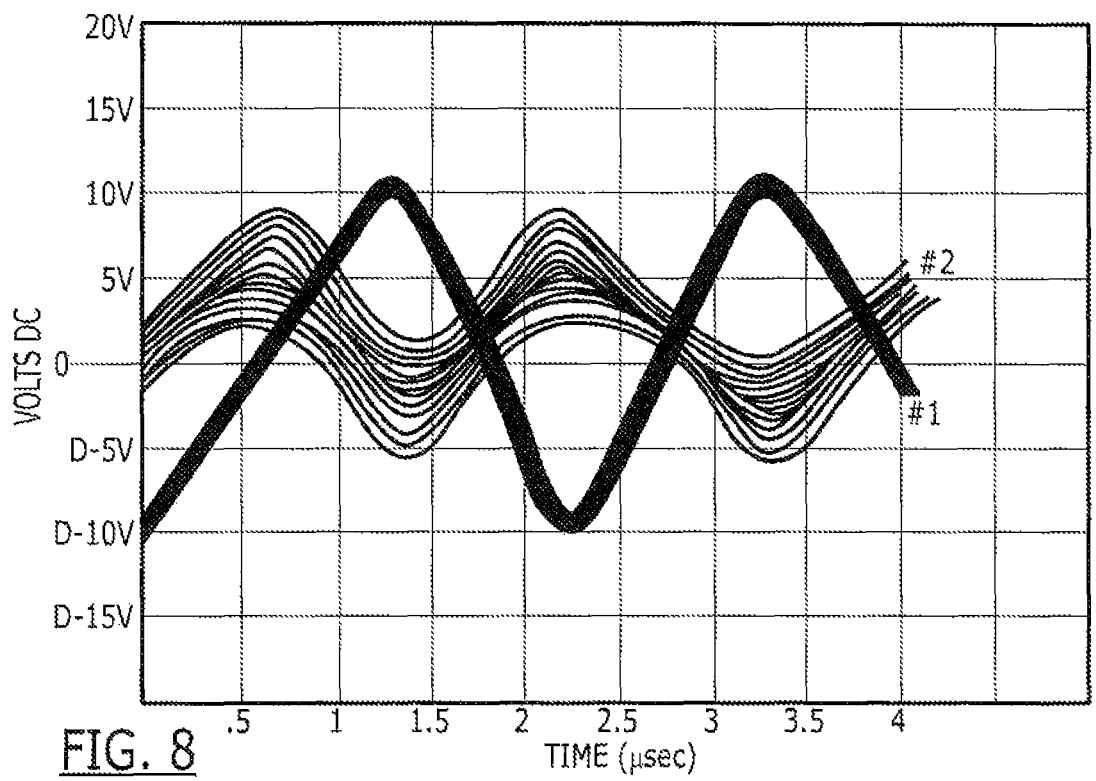
FIG. 8 is a frequency calculation of the first chamber in the plasma device.
Figure 9:
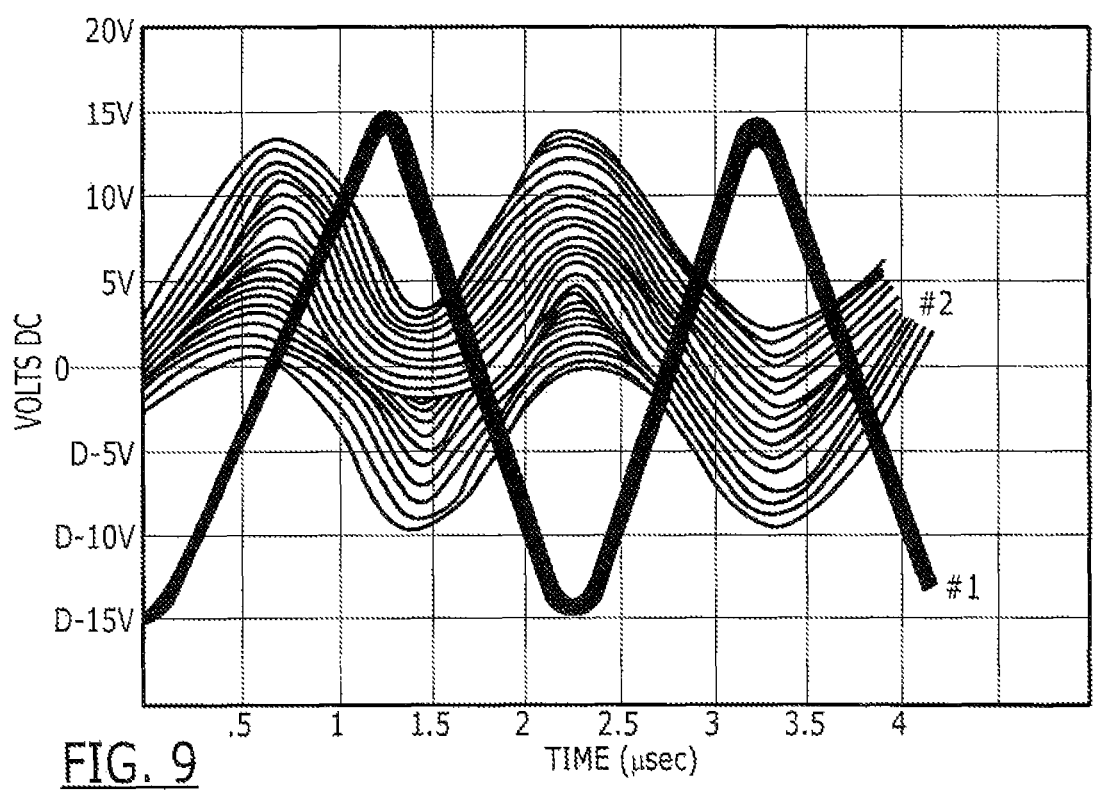
FIG. 9 is a frequency calculation of the second chamber in the plasma device.
Figure 10:
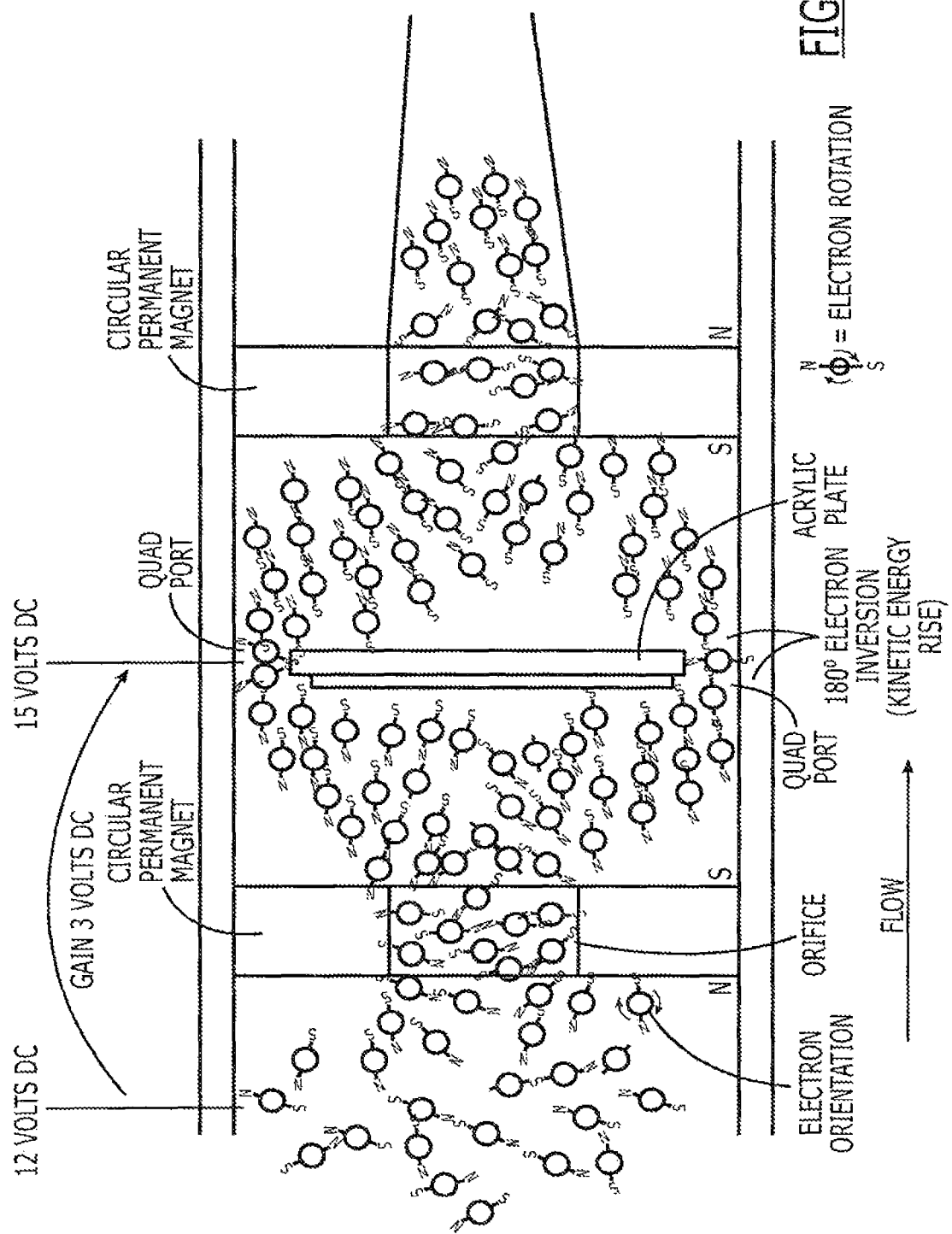
FIG. 10 illustrates electron flow and orientation in the second plasma compression chamber.

FIGS. 8 and 9 are frequency calculations of the first 62 and second 80 chambers in the plasma device 60. For FIG. 8, frequency #1=12 V at μsec=500 kHz; frequency #2=3 to 9 V at 1.5 to 2 μsec=750-500 kHz. The dielectric static voltage=150 kV. For FIG. 9, frequency #1=15 V at 2 μsec=500 kHz; frequency #2=0 to 13 V at 1.5 to 2 μsec=750-500 kHz. The dielectric static voltage=150 kV. In the second chamber 80, there is an increase in energy by 3 Vdc at the plasma quad ports 70. There is an energy gain, as the electron spin rotation is changed 180° at the ports 70 in the compressed magnetic field, allowing a kinetic energy increase for the plasma flow, as illustrated schematically in FIG. 10.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the device illustrated and described herein are by way of example, and the scope of the invention is not limited to the exact details of construction and use.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A device comprising:
 a radio frequency (RF) power source;
 an electrode positioned in electrical communication with the RF power source, wherein the electrode is configured to release multi-frequency energy;
 a magnetic assembly positioned downstream of the electrode, wherein the magnetic assembly is configured to provide a magnetic field;
 a grid positioned in the compressed magnetic field and in electrical communication with the RF power source, wherein the grid is in frequency harmony with the electrode; and
 wherein the electrode is configured to energize a working gas, and wherein the grid is configured to further energize the working gas to produce a multi-frequency cold plasma.

2. The device of claim 1, further comprising:
 a housing having an inner space; and
 an input port configured to introduce the working gas into the inner space upstream of the electrode,
 wherein the electrode, the magnetic assembly, and the grid are positioned within the inner space.

3. The device of claim 2, wherein the housing defines an orifice downstream of the grid, wherein the orifice is configured to permit the multi-frequency cold plasma to exit the housing.

4. The device of claim 1, wherein the magnetic assembly comprises:
 a first magnet positioned within the inner space downstream of the electrode; and
 a second magnet positioned within the inner space downstream of the first magnet.

5. The device of claim 4, wherein the grid is positioned between the first and second magnets.

6. The device of claim 5, wherein the first and second magnets are toroidal magnets.

7. The device of claim 5, wherein the first and second magnets form a magnetic compression chamber.

8. The device of claim 5, wherein the first magnet and the second magnet are magnetically aligned in a south-to-south alignment.

9. The device of claim 5, wherein a first pole of the first magnet and a first pole of the second magnet are equidistant from the grid.

10. The device of claim 5, further comprising:
 a support plate positioned between the first and the second magnets and configured to provide support for the grid, the support plate having an aperture therethrough.

11. The device of claim 5, wherein the grid comprises:
 a central capacitance element in electrical communication with the RF power source; and
 a plurality of conductors, each of the plurality of conductors having an outer capacitance element affixed at opposed ends, the plurality of conductors arrayed about the central capacitance element, and an outermost conductor of the plurality of conductors in electrical communication with the RF power source.

12. The device of claim 1, wherein the grid comprises:
   a central capacitance element in electrical communication with the RF power source; and
   a plurality of conductors, each of the plurality of conductors having an outer capacitance element affixed at opposed ends, the plurality of conductors arrayed about the central capacitance element, and an outermost conductor of the plurality of conductors in electrical communication with the RF power source.

13. The device of claim 12, wherein the central and the outer capacitance elements comprise metal-coated brass spheres.

14. The device of claim 13, wherein the metal-coated brass spheres of the outer capacitance elements have diameters increasing with increasing radial distance from the metal-coated brass sphere of the central capacitance element, and wherein the metal-coated brass sphere of the central capacitance element has a diameter greater than an outer capacitance element most closely adjacent thereto.

15. The device of claim 1, wherein the electrode comprises a plurality of electrode plates.

16. The device of claim 15, wherein a surface area of a first one of the plurality of electrode plates exceeds a surface area of a second one of the plurality of electrode plates.

17. The device of claim 15, wherein the plurality of electrode plates have a common axis, and wherein each of the plurality of electrode plates has a different thickness.

18. The device of claim 15, wherein the electrode further comprises a support rod in signal communication with the RF power source, the support rod extending through each electrode plate of the plurality of electrode plates.

19. The device of claim 1, wherein the grid comprises a plurality of elements, wherein at least two of the plurality of elements are configured to resonate at difference frequencies.

20. A method comprising:
   energizing, by an electrode, a working gas, wherein the electrode is positioned in electrical communication with a radiofrequency (RF) power source, wherein the electrode releases multi-frequency energy to energize the working gas, wherein a magnetic assembly is positioned downstream of the electrode, wherein the magnetic assembly provides a magnetic field, wherein a grid is positioned in the compressed magnetic field and in electrical communication with the RF power source, wherein the grid is in frequency harmony with the electrode; and
   further energizing, by the grid, the working gas, thereby producing a multi-frequency cold plasma.

* * * * *